US007816352B2

(12) United States Patent
Carson et al.

(10) Patent No.: US 7,816,352 B2
(45) Date of Patent: Oct. 19, 2010

(54) APOPTOSIS INHIBITORS

(75) Inventors: Dennis A. Carson, La Jolla, CA (US); Howard B. Cottam, Escondido, CA (US); Sylvie Barchéchath, Geneva (CH); Mary Patricia Corr, San Diego, CA (US)

(73) Assignee: The Regents of The University of California, Oakland, CA (US)

( * ) Notice: Subject to any disclaimer, the term of this patent is extended or adjusted under 35 U.S.C. 154(b) by 67 days.

(21) Appl. No.: 11/885,463

(22) PCT Filed: Mar. 10, 2006

(86) PCT No.: PCT/US2006/008911
§ 371 (c)(1),
(2), (4) Date: May 5, 2008

(87) PCT Pub. No.: WO2006/099301
PCT Pub. Date: Sep. 21, 2006

(65) Prior Publication Data
US 2008/0280903 A1    Nov. 13, 2008

Related U.S. Application Data

(60) Provisional application No. 60/660,839, filed on Mar. 10, 2005.

(51) Int. Cl.
| A61K 31/535 | (2006.01) |
| A61K 31/47 | (2006.01) |
| A61K 31/497 | (2006.01) |
| C07D 213/56 | (2006.01) |
| C07D 217/00 | (2006.01) |
| C07D 215/38 | (2006.01) |

(52) U.S. Cl. .............. 514/235.2; 514/253.11; 514/235.5; 514/357; 514/343; 514/253.06; 514/314; 514/311; 514/307; 514/253.05; 544/128; 544/363; 544/360; 544/124; 546/276.4; 546/159; 546/201; 546/145; 546/338

(58) Field of Classification Search .............. 546/276.4; 514/187
See application file for complete search history.

(56) References Cited

FOREIGN PATENT DOCUMENTS

WO   WO-2006/099301 A2   9/2006
WO   WO-2006/099301 A3   9/2006

(Continued)

OTHER PUBLICATIONS

Gupta, et. al., Synthesis and reactions of pyridinium iodides of substituted acetophenones. Journal of the Indian Chemical Society, 1971, vol. 48, No. 9.*

(Continued)

*Primary Examiner*—Janet L Andres
*Assistant Examiner*—Binta M Robinson
(74) *Attorney, Agent, or Firm*—Schwegman, Lundberg & Woessner, P.A.

(57) ABSTRACT

The present invention provides compounds that act as selective agents to protect against unintentional cell death or tissue damage and can relieve side effects of cancer treatment such as, for example, oral mucositis, hair loss, diarrhea due to damage to the gastrointestinal epithelium, and myelosuppression. In addition, these compounds can be used to prevent premature cell death when the cell death is caused by signals from damaged cells, for example, signals generated as the result of a traumatic incident or an ischemic episode.

30 Claims, 1 Drawing Sheet

FOREIGN PATENT DOCUMENTS

WO  WO-2006099301 A2  9/2006

OTHER PUBLICATIONS

Hcaplus 1972:46046 abstract, "Synthesis and reactions of pyridinium iodides of substituted acetophenones", Gupta et. al., 1971.*

Karljikovic et. al., "Determination of Acidic Constants of some Phenyl-hydroxyiminoethyl Quinolinium Compounds", Monatshefte fur Chemie 117, 661-670 (1986).*

Hcaplus 1988:33102 Abstract, "Silver electrode in direct potentiometric determination of 4'- and 6'-methyl derivatives of 1-(2-phenyl-2-hydroxyiminoethyl)-1-quinolinium chloride", Karljikovic-Rajic et. al., (1987).*

Patani et. al., "Bioisosterism: A Rational Approach in Drug Design" Chem. Rev. 1996, 96, 3147-3176.*

Hcaplus 2005:244454, "Quinolinium salt as a potent inhibitor of lymphocyte apoptosis", Barchechath et. al., Bioorganic & Medicinal Chemistry Letters article accepted Feb. 16, 2005.*

Barchechath et. al., "Quinolinium salt as a potent inhibitor of lymphocyte apoptosis", Bioorganic & Medicinal Chemistry Letters 15 (2005), pp. 1785-1788.*

Patani et. al., "Bioisosterism: A Rational Approach in Drug Design", Chem. Rev. 1996, 96, pp. 3147-3176.*

Artyomov, V. A., et al., "Synthesis of Imidazo [1,2-a} pyridines from Pyridines and p-Bromophenacyl Bromide O-Methyloxime", *Synthesis*; 8, (1996),927-929.

Fico, G. , et al., "RAPD analysis and flavonoid composition of Aconitum as an aid for taxonomic discrimination", *Biochemical Systematics and Ecology*, 31(3), (2003),293-301.

Gupta, D. , et al., "Synthesis and Reactions of pyridinium iodides of substituted acetophenones", *Journal of the Indian Chemical Society*; 48(9), (1971).

Karljikovic-Rajic, K. , et al., "Silver Electrode in Direct Potentiometric Determination of 4'- and 6-methyl derivatives of 1-(2-phenyl-2-hydroxyiminoethyl)-1-quinolinium chloride", *Journale de Pharmacie de Belgique*.

Artyomov, V. A., et al., "Synthesis of Imidazo[1,2-alpha]pyridines from Pyridines and pBromophenacyl Bromide O-Methyloxime", *Synthesis*, 8, (1996), 927-929.

Fico, G. , et al., "RAPD analysis and flavonoid composition of Aconitum as an aid for Taxonomic discrimination", *Biochemical Systematics and Ecology*, 31(3), (2003), Abstract Only, Chemical Abstracts Doc. No. 140:90496, 3 p.

Gupta, D. , et al., "Synthesis and Reactions of pyridinium iodides of substituted acetophenones", *Journal of the Indian Chemical Society*; 48(9), (1971), Abstract Only, Chemical Abstracts Doc. No. 76:46046, 2 p.

Karljikovic-Rajic, K. , et al., "Silver Electrode in Direct Potentiometric Determination of 4'- and 6'-methyl derivatives of 1-(2-phenyl-2-hydroxyiminoethyl)-1-quinolinium chloride", *Journale de Pharmacie de Beligique*, 42(4), (1987), Abstract Only, Chemical Abstracts Doc. No. 108:33102, 2 p.

* cited by examiner

APOPTOSIS INHIBITORS

PRIORITY OF INVENTION

This application is a nationalization under 35 U.S.C. 371 of PCT/US2006/008911, filed Mar. 10, 2006 and published as WO 2006/099301, on Sep. 21, 2006, which claims the benefit of priority under 35 U.S.C. §119(e) to U.S. Provisional Patent Application Ser. No. 60/660,839, filed Mar. 10, 2005, which application is hereby incorporated by reference for all purposes.

GOVERNMENT FUNDING

The invention described herein was made with government support under Grant No. AI57436 awarded by the National Institutes of Health. The United States Government has certain rights in the invention.

BACKGROUND OF THE INVENTION

Cancer is a leading cause of death in the United States. For example in 1998, an estimated 185,000 men were diagnosed with prostate cancer, and more than 39,000 men died of the disease. See, S. H. Landis et al., *CA Cancer J. Clin.* 48, 6, 1998. Although survival rates for cancer patients are good in patients that are diagnosed early, the treatment usually used for cancer is often indiscriminant attacking both normal cells and cancerous cells. Cytotoxic agents (chemotherapy) or radiation therapy are commonly used treatments for cancer. For example, despite modern advances in focusing external beam radiation to the tumor mass, some normal tissues are usually included in the radiation field.

Cytotoxic agents and radiation can kill both normal and malignant tissues, primarily by triggering apoptosis. Chemoprevention of cell death is an important goal for pharmacologic intervention in a variety of clinical settings, including ischemia and side effects from cancer treatment. Drugs that inhibit apoptosis in normal cells/tissues within the treatment area are of great value. Pharmacologic agents that have been used to protect cells from ionizing radiation fall into three major categories. First, sulfhydryl containing agents, metal chelators, and various anti-oxidants, which can inhibit the propagation of free radical reactions. Second, exogenous growth and survival factors, which can stimulate the endogenous synthesis of cell-protective molecules. Third, chemical inhibitors of essential proteins in the apoptosis cascade, which can delay cell suicide until the damage is repaired.

Recently, a small molecule, 2-(2-imino-4,5,6,7-tetrahydro-benzothiazol-3-yl)-1-p-tolyl-ethanone hydrobromide, 1, was identified from a broad screen of 10,000 compounds in an assay that assessed the ability to inhibit cell death from γ-radiation (See Komarov, P. G., et al. *Science,* 285:1733-1737, 1999.) This compound was designated pifithrin-α, (PFTα, PFT-alpha).

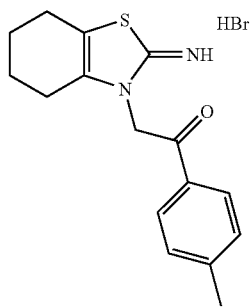

PFT-alpha, 1

This compound has been shown to protect normal cells from the lethal effects of some cancer treatments. For example, cells pre-incubated with PFTα, and then exposed to γ-radiation, showed a decreased in apoptosis. PFTα also reduced mortality after γ-radiation of mice.

In addition, there are other causes of cell death such as, for example, ischemia. The ischemia can be caused by several sources such as, stroke, heart attack and traumas.

Currently, there is a need for novel, potent, and selective agents to selectively protect against unintentional cell death or tissue damage, caused by cancer treatment and from other side effects of cancer treatment such as, oral mucositis, hair loss, diarrhea due to damage to the gastrointestinal epithelium, and myelosuppression.

SUMMARY OF THE INVENTION

The present invention provides compounds that act as selective agents to protect against unintentional cell death or tissue damage and can relieve side effects of cancer treatment such as, for example, oral mucositis, hair loss, diarrhea due to damage to the gastrointestinal epithelium, and myelosuppression. In addition, these compounds can be used to prevent premature cell death when the cell death is caused by signals from damaged cells, for example, signals generated as the result of a traumatic incident or an ischemic episode.

Accordingly, the present invention provides compounds of formula (I):

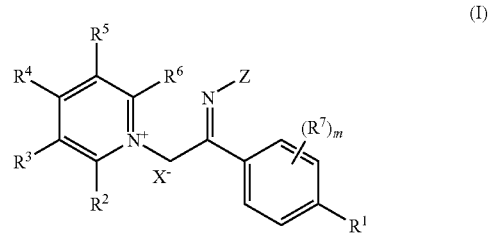

(I)

wherein $R^1$ is —$N(R^b)(R^c)$, $(C_1-C_6)$alkyl, $(C_3-C_7)$cycloalkyl, aryl, or heteroaryl, or a 5-6 membered heterocyclic ring, optionally comprising 1, 2, or 3 —$N(R^b)$—, nonperoxide O or S atoms;

wherein $R^1$ is optionally substituted with 1, 2, 3, 4, or 5, preferably 1 or 2, halo, —$CF_3$, hydroxy, cyano, $(C_1-C_6)$alkyl, $(C_1-C_6)$alkoxy, $(C_2-C_7)$alkanoyl, $(C_2-C_7)$alkanoyloxy, —$CO_2R^a$, $(C_3-C_7)$cycloalkyl, $(C_2-C_6)$alkanoyl, $(C_2-C_6)$alkenyl, or aryl groups;

$R^1$, $R^3$, $R^4$, $R^5$, and $R^6$ are independently hydrogen, halo, hydroxy, cyano, —$N(R^b)(R^c)$, $S(R^a)$, —$NO_2$, $(C_1-C_6)$alkyl, $(C_1-C_6)$alkoxy, $(C_2-C_6)$alkynyl, $(C_2-C_6)$alkenyl, $(C_2-C_7)$alkanoyl, $(C_2-C_7)$alkanoyloxy, or $(C_3-C_7)$cycloalkyl; or either $R^2$ and $R^3$ or either $R^3$ and $R^4$ taken together with the atoms to which they are attached form a benzo ring, optionally substituted with 1, 2, 3, or 4 $R^6$ groups, or either $R^2$ and $R^3$ or either $R^3$ and $R^4$ are a 3, 4, or 5 membered alkylene chain (e.g., —$CH_2$—, —$CH_2CH_2$—, —$CH_2CH_2CH_2$—, or —$CH_2CH_2CH_2CH_2$—) 3, 4, or 5 membered alkenylene, or methylenedioxy that is fused to the ring;

each $R^7$ is independently hydrogen, halo, hydroxy, cyano, —$N(R^b)(R^c)$, —$S(R^a)$, —$NO_2$, $(C_1-C_6)$alkyl, $(C_1-C_6)$alkoxy, $(C_2-C_6)$alkynyl, $(C_2-C_6)$alkenyl, $(C_2-C_7)$alkanoyl, $(C_2-C_7)$alkanoyloxy, or $(C_3-C_7)$cycloalkyl;

wherein each $R^a$ is independently hydrogen, $(C_1-C_3)$alkyl, phenyl, benzyl, or phenethyl; and wherein $R^b$ and $R^c$ are each independently hydrogen, $(C_1-C_3)$alkyl, $(C_2-C_4)$alkanoyl, phenyl, benzyl, or phenethyl; or $R^b$ and $R^c$ together with the nitrogen to which they are attached are a 5 or 6 membered heterocyclic ring, optionally comprising 1, 2, or 3 —N($R^a$)—, nonperoxide O or S atoms, preferably pyrrolidinyl, piperazinyl, piperidinyl, or morpholinyl;

Z is —$OR^a$, —$SR^a$, or —N($R^b$)($R^c$); m is 0, 1, 2, 3, or 4;

$X^-$ is a pharmaceutically acceptable counterion.

The present invention also provides pharmaceutical salts of the compounds of formula (I).

Additionally, the invention provides a therapeutic method for chemoprevention of premature cell death or treating a condition or symptom in a mammal, such as a human, wherein the chemoprevention of cell death is desired. The method comprises administering to a mammal in need of such therapy, an effective amount of a compound of formula (I), or a pharmaceutically acceptable salt thereof.

The invention provides a compound of formula (I) for use in medical therapy, preferably for use in prevention of cell death or tissue damage as well as the use of a compound of formula I for the manufacture of a medicament for the prevention of cell death or tissue damage in a mammal, such as a human, which is subject to trauma or cancer treatment.

DETAILED DESCRIPTION OF THE INVENTION

Figure 1:
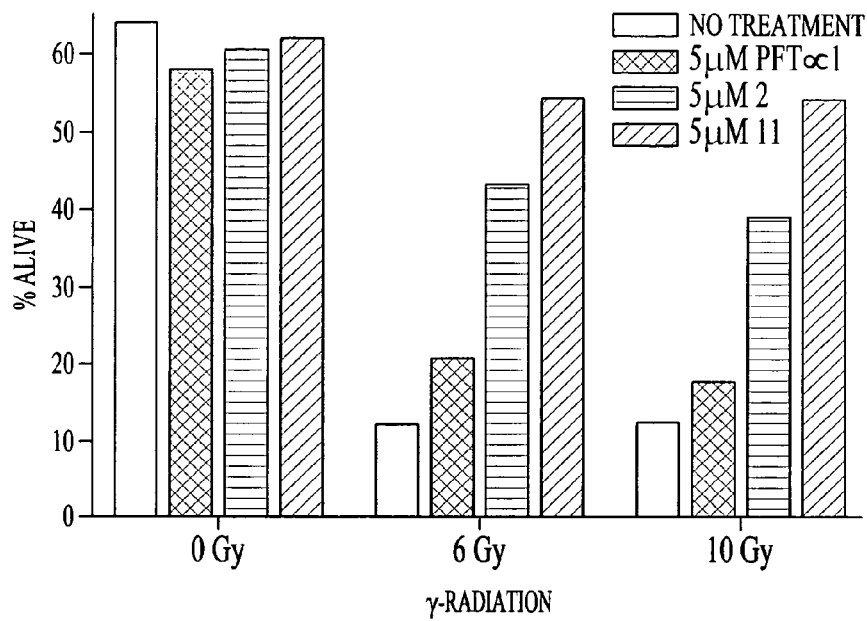
FIG. 1 is a graphical representation of the comparative radioprotective effects of 1 (PFTα), 2, and 11 at 5 μM.

The pyridinium and quinolinium salts and related compounds of the invention, formula (I), have an ability to inhibit glucocorticoid-induced and radiation-induced apoptosis in murine thymocytes. Thus, the compounds of the invention show a chemoprotective effect and can prevent cell death caused by trauma, ischemia, and side effects of cancer therapy.

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

A "pharmaceutically acceptable counterion" refers to an ion having a charge opposite to that of the substance with which it is associated and that is pharmaceutically acceptable. Representative examples include, but are not limited to, fluoride, chloride, bromide, iodide, hydroxide, sulfate, phosphate, carbonate, methanesulfonate, p-tolylsulfonate, trifluoroacetate, acetate, citrate, other acid anions, and the like.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine nicotine agonist activity using the standard tests described herein, or using other similar tests which are well known in the art.

Specific and preferred values listed below for radicals, substituents, and ranges, are for illustration only; they do not exclude other defined values or other values within defined ranges for the radicals and substituents Specifically, ($C_1$-$C_6$)alkyl can be methyl, ethyl, propyl, isopropyl, butyl, iso-butyl, sec-butyl, pentyl, 3-pentyl, or hexyl; ($C_3$-$C_7$)cycloalkyl can be cyclopropyl, cyclobutyl, cyclopentyl, or cyclohexyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$)alkanoyl can be acetyl, propanoyl or butanoyl; halo($C_1$-$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; ($C_2$-$C_6$)alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

The term "($C_3$-$C_5$)alkylene" refers to a saturated, branched or straight chain or cyclic hydrocarbon radical of 3-5 carbon atoms, and having two monovalent radical centers derived by the removal of two hydrogen atoms from the same or two different carbon atoms of a parent alkane. Typical alkylene radicals include, but are not limited to, methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

The term "($C_3$-$C_5$)alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CHCH—).

A specific value for $R^1$ is N($R^b$)($R^c$), ($C_1$-$C_4$)alkyl, or aryl.

Another specific value for $R^1$ is —N($R^b$)($R^c$), methyl, ethyl, propyl, or phenyl.

Another specific value for $R^1$ is methyl, pyrrolidinyl, piperizinyl, piperidinyl, or morpholinyl.

Another specific value for $R^1$ is methyl, or pyrrolidinyl.

Another specific value for $R^1$ is pyrrolidinyl.

Another specific value for $R^1$ is methyl.

A specific value for $R^2$ is hydrogen, ($C_1$-$C_4$)alkyl, ($C_1$-$C_4$) alkoxy, halo, hydroxy, cyano, or —N($R^b$)($R^c$).

Another specific value for $R^2$ is hydrogen, hydroxy, methyl, ethyl, propyl, methoxy, ethoxy, chloro, bromo, or pyrrolidinyl.

Another specific value for $R^2$ is hydrogen, hydroxy, methyl, ethyl, methoxy, chloro, or bromo.
Another specific value for $R^2$ is hydrogen, hydroxy, methyl, ethyl, or methoxy.
Another specific value for $R^2$ is hydrogen, or methyl.
Another specific value for $R^2$ is hydrogen.
A specific value for $R^3$ is hydrogen, $(C_1-C_4)$alkyl, $(C_1-C_4)$alkoxy, halo, hydroxy, cyano, or —$N(R^b)(R^c)$.
Another specific value for $R^3$ is hydrogen, hydroxy, methyl, ethyl, propyl, methoxy, ethoxy, chloro, bromo, or pyrrolidinyl.
Another specific value for $R^3$ is hydrogen, hydroxy, methyl, ethyl, methoxy, chloro, or bromo.
Another specific value for $R^3$ is hydrogen, hydroxy, methyl, ethyl, or methoxy.
Another specific value for $R^3$ is hydrogen, or methyl.
Another specific value for $R^3$ is hydrogen.
A specific value for $R^4$ hydrogen, $(C_1-C_4)$alkyl, $(C_1-C_4)$alkoxy, halo, hydroxy, cyano, or $N(R^b)(R^c)$.
Another specific value for $R^4$ is hydrogen, hydroxy, methyl, ethyl, propyl, methoxy, ethoxy, chloro, bromo, or pyrrolidinyl.
Another specific value for $R^4$ is hydrogen, hydroxy, methyl, ethyl, methoxy, chloro, or bromo.
Another specific value for $R^4$ is hydrogen, hydroxy, methyl, ethyl, or methoxy.
Another specific value for $R^4$ is hydrogen, or methyl.
Another specific value for $R^4$ is hydrogen.
A specific value for $R^5$ is hydrogen, $(C_1-C_4)$alkyl, $(C_1-C_4)$alkoxy, halo, hydroxy, cyano, or —$N(R^b)(R^c)$.
Another specific value for $R^5$ is hydrogen, hydroxy, methyl, ethyl, propyl, methoxy, ethoxy, chloro, bromo, or pyrrolidinyl.
Another specific value for $R^5$ is hydrogen, hydroxy, methyl, ethyl, methoxy, chloro, or bromo.
Another specific value for $R^5$ is hydrogen, hydroxy, methyl, ethyl, or methoxy.
Another specific value for $R^5$ is hydrogen, or methyl.
Another specific value for $R^5$ is hydrogen.
A specific value for $R^6$ is hydrogen, $(C_1-C_4)$alkyl, $(C_1-C_4)$alkoxy, halo, hydroxy, cyano, or —$N(R^b)(R^c)$.
Another specific value for $R^6$ is hydrogen, hydroxy, methyl, ethyl, propyl, methoxy, ethoxy, chloro, bromo, or pyrrolidinyl.
Another specific value for $R^6$ is hydrogen, hydroxy, methyl, ethyl, methoxy, chloro, or bromo.
Another specific value for $R^6$ is hydrogen, hydroxy, methyl, ethyl, or methoxy.
Another specific value for $R^6$ is hydrogen, or methyl.
Another specific value for $R^6$ is hydrogen.
A specific value for $R^2$ and $R^3$ taken together with the atoms to which they are attached form a benzo ring.
A specific value for $R^3$ and $R^4$ taken together with the atoms to which they are attached form a benzo ring.
A specific value for $R^7$ is hydrogen $(C_1-C_4)$alkyl, $(C_1-C_4)$alkoxy, halo, hydroxy, cyano, or —$N(R^b)(R^c)$.
Another specific value for $R^7$ is hydrogen, hydroxy, methyl, ethyl, propyl, methoxy, ethoxy, fluoro, chloro, bromo, or pyrrolidinyl.
Another specific value for $R^7$ is hydrogen, hydroxy, methyl, ethyl, methoxy, fluoro, chloro, or bromo.
Another specific value for $R^7$ is hydrogen, hydroxy, methyl, ethyl, fluoro, or methoxy.
Another specific value for $R^7$ is hydrogen, fluoro, or methyl.
Another specific value for $R^7$ is fluoro.
Another specific value for $R^7$ is hydrogen.

A specific value for m is 0, 1, 2.
Another specific value for m is 0, 1.
A specific value for $R^a$ is hydrogen, $(C_1-C_4)$alkyl, phenyl, or benzyl.
Another specific value for $R^a$ is hydrogen, methyl, ethyl, or phenyl.
Another specific value for $R^a$ is hydrogen, or methyl.
Another specific value for $R^a$ is hydrogen.
A specific value for $R^b$ is hydrogen, $(C_1-C_4)$alkyl, phenyl, acetyl, propionyl, butanoyl, or benzyl.
Another specific value for $R^b$ is hydrogen, methyl, ethyl, phenyl, or acetyl.
Another specific value for $R^b$ is hydrogen, or methyl.
Another specific value for $R^b$ is hydrogen.
A specific value for $R^c$ is hydrogen, $(C_1-C_4)$alkyl, phenyl, acetyl, propionyl, butanoyl, or benzyl.
Another specific value for $R^c$ is hydrogen, methyl, ethyl, phenyl, or acetyl.
Another specific value for $R^c$ is hydrogen, or methyl.
Another specific value for $R^c$ is hydrogen.
A specific value for —$N(R^b)(R^c)$, is pyrrolidinyl, piperizinyl, piperidinyl, or morpholinyl.
Another specific value for —$N(R^b)(R^c)$, is pyrrolidinyl.
Another specific value for —$N(R^b)(R^c)$, is morpholinyl.
A specific value for Z is hydroxy, methoxy, ethoxy, —NH($OCH_3$), or —NH($OCH_2CH_3$).
A specific value for Z is methoxy.
A specific X is chloride, bromide, hydroxide, sulfate, phosphate, carbonate, acetate, or citrate.
Another specific $X^-$ is chloride, bromide, carbonate, or acetate.
Another specific $X^-$ is bromide.
A specific group of compounds are compounds of formula (Ia) as disclosed in Table 1.

TABLE 1

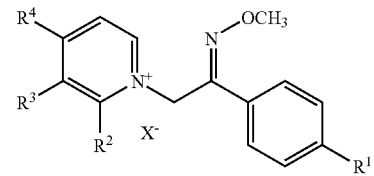

(Ia)

| Compound | $R^1$ | $R^2$ | $R^3$ | $R^4$ |
|---|---|---|---|---|
| 101 | H | H | H | H |
| 102 | H | H | H | —$CH_3$ |
| 103 | H | H | —$CH_3$ | H |
| 104 | H | H | —$CH_3$ | —$CH_3$ |
| 105 | H | —$CH_3$ | H | H |
| 106 | H | —$CH_3$ | H | —$CH_3$ |
| 107 | H | —$CH_3$ | —$CH_3$ | —$CH_3$ |
| 108 | H | —$CH_3$ | —$CH_3$ | H |
| 11 | Pyrrolidinyl | H | H | H |
| 110 | Pyrrolidinyl | H | H | —$CH_3$ |
| 111 | Pyrrolidinyl | H | —$CH_3$ | H |
| 112 | Pyrrolidinyl | H | —$CH_3$ | —$CH_3$ |
| 113 | Pyrrolidinyl | —$CH_3$ | H | H |
| 114 | Pyrrolidinyl | —$CH_3$ | H | —$CH_3$ |
| 115 | Pyrrolidinyl | —$CH_3$ | —$CH_3$ | —$CH_3$ |
| 116 | Pyrrolidinyl | —$CH_3$ | —$CH_3$ | H |
| 117 | Methyl | H | H | H |
| 118 | Methyl | H | H | —$CH_3$ |
| 119 | Methyl | H | —$CH_3$ | H |
| 120 | Methyl | H | —$CH_3$ | —$CH_3$ |
| 121 | Methyl | —$CH_3$ | H | H |
| 122 | Methyl | —$CH_3$ | H | —$CH_3$ |
| 123 | Methyl | —$CH_3$ | —$CH_3$ | —$CH_3$ |
| 124 | Methyl | —$CH_3$ | —$CH_3$ | H |

TABLE 1-continued (Ia)

| Compound | R¹ | R² | R³ | R⁴ |
|---|---|---|---|---|
| 125 | Piperizinyl | H | H | H |
| 126 | Piperizinyl | H | H | —CH₃ |
| 127 | Piperizinyl | H | —CH₃ | H |
| 128 | Piperizinyl | H | —CH₃ | —CH₃ |
| 129 | Piperizinyl | —CH₃ | H | H |
| 130 | Piperizinyl | —CH₃ | H | —CH₃ |
| 131 | Piperizinyl | —CH₃ | —CH₃ | —CH₃ |
| 132 | Piperizinyl | —CH₃ | —CH₃ | H |
| 133 | Piperidinyl | H | H | H |
| 134 | Piperidinyl | H | H | —CH₃ |
| 135 | Piperidinyl | H | —CH₃ | H |
| 136 | Piperidinyl | H | —CH₃ | —CH₃ |
| 137 | Piperidinyl | —CH₃ | H | H |
| 138 | Piperidinyl | —CH₃ | H | —CH₃ |
| 139 | Piperidinyl | —CH₃ | —CH₃ | —CH₃ |
| 140 | Piperidinyl | —CH₃ | —CH₃ | H |
| 142 | Morpholinyl | H | H | H |
| 143 | Morpholinyl | H | H | —CH₃ |
| 144 | Morpholinyl | H | —CH₃ | H |
| 145 | Morpholinyl | H | —CH₃ | —CH₃ |
| 146 | Morpholinyl | —CH₃ | H | H |
| 147 | Morpholinyl | —CH₃ | H | —CH₃ |
| 148 | Morpholinyl | —CH₃ | —CH₃ | —CH₃ |
| 149 | Morpholinyl | —CH₃ | —CH₃ | H |

A specific group of compounds are compounds of formula (IIa) wherein

TABLE 2

(IIa)

| Compound | R¹ | R⁴ | R⁵ |
|---|---|---|---|
| 201 | H | H | H |
| 202 | H | H | —CH₃ |
| 203 | H | —CH₃ | H |
| 204 | H | —CH₃ | —CH₃ |
| 205 | Pyrrolidinyl | H | H |
| 206 | Pyrrolidinyl | H | —CH₃ |
| 207 | Pyrrolidinyl | —CH₃ | H |
| 208 | Pyrrolidinyl | —CH₃ | —CH₃ |
| 209 | Methyl | H | H |
| 210 | Methyl | H | —CH₃ |
| 211 | Methyl | —CH₃ | H |
| 212 | Methyl | —CH₃ | —CH₃ |
| 213 | Piperizinyl | H | H |
| 214 | Piperizinyl | H | —CH₃ |
| 215 | Piperizinyl | —CH₃ | H |
| 216 | Piperizinyl | —CH₃ | —CH₃ |
| 217 | Piperidinyl | H | H |
| 218 | Piperidinyl | H | —CH₃ |
| 219 | Piperidinyl | —CH₃ | H |
| 220 | Piperidinyl | —CH₃ | —CH₃ |

TABLE 2-continued (IIa)

| Compound | R¹ | R⁴ | R⁵ |
|---|---|---|---|
| 221 | Morpholinyl | H | H |
| 222 | Morpholinyl | H | —CH₃ |
| 223 | Morpholinyl | —CH₃ | H |
| 224 | Morpholinyl | —CH₃ | —CH₃ |

A specific group of compounds are compounds of formula (III) wherein

TABLE 3

(III)

| Compound | R¹ | R² | R⁵ |
|---|---|---|---|
| 301 | H | H | H |
| 302 | H | H | —CH₃ |
| 303 | H | —CH₃ | H |
| 304 | H | —CH₃ | —CH₃ |
| 305 | Pyrrolidinyl | H | H |
| 306 | Pyrrolidinyl | H | —CH₃ |
| 307 | Pyrrolidinyl | —CH₃ | H |
| 308 | Pyrrolidinyl | —CH₃ | —CH₃ |
| 309 | Methyl | H | H |
| 310 | Methyl | H | —CH₃ |
| 311 | Methyl | —CH₃ | H |
| 312 | Methyl | —CH₃ | —CH₃ |
| 313 | Piperizinyl | H | H |
| 314 | Piperizinyl | H | —CH₃ |
| 315 | Piperizinyl | —CH₃ | H |
| 316 | Piperizinyl | —CH₃ | —CH₃ |
| 317 | Piperidinyl | H | H |
| 318 | Piperidinyl | H | —CH₃ |
| 319 | Piperidinyl | —CH₃ | H |
| 320 | Piperidinyl | —CH₃ | —CH₃ |
| 321 | Morpholinyl | H | H |
| 322 | Morpholinyl | H | —CH₃ |
| 323 | Morpholinyl | —CH₃ | H |
| 324 | Morpholinyl | —CH₃ | —CH₃ |

In a specific group of compounds having formula (Ia) $R^2$, $R^3$ and $R^4$ are hydrogen, methyl or ethyl. Preferably one of $R^2$, $R^3$ and $R^4$ is hydrogen.

Processes for preparing compounds of formula I are provided as further embodiments of the invention and are illustrated by the following procedures in which the meanings of the generic radicals are as given above unless otherwise qualified. The compounds of the invention can generally be prepared as illustrated in Schemes 1 and 2 below. Starting materials can be prepared by procedures described in these schemes, procedures described in the General methods below or by procedures that would be well known to one of ordinary skill in organic chemistry. The variables used in Schemes 1 and Scheme 2 are as defined herein or as in the claims.

The appropriate quinoline or pyridine is treated with a suitable oxime or acetophenone (having a leaving group, Lv), in refluxing acetone to provide the coupled product. If the acetophenone is used this compound can be converted to provide the appropriate —N-Z group using techniques known to a person skilled in the art.

Scheme 1

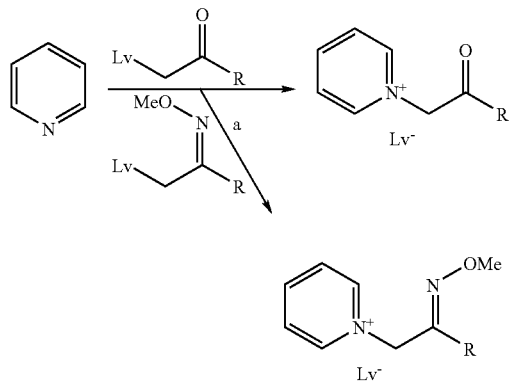

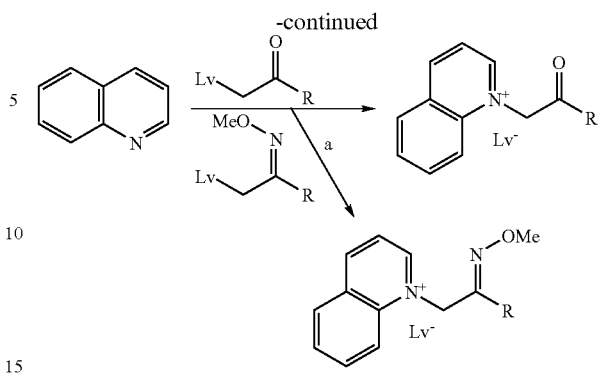

For a specific example see scheme 2. Quinoline is treated with 2-bromo-1-p-tolylethanone O-methyl oxime (3) in refluxing acetone to provide 1-(2-methoxyimino-2-p-tolyl-ethyl)quinolinium bromide (4). Proton NMR experiments, including NOE, indicated that 4 has the E-configuration, consistent with results of earlier studies using a para-bromo-substituted O-methyl oxime for alkylation of several quinolines and pyridines. No other isomer was isolated or detected in the reaction. A comparison of the cytoprotective activity of 4 with 1 following in vitro dexamethasone treatment of mouse thymocytes showed 4 to be significantly more protective than 1 with $EC_{50}$s of 0.35 and 4.4 μM, respectively. Similarly, the reaction can be conducted using pyridine as the starting material.

Scheme 2

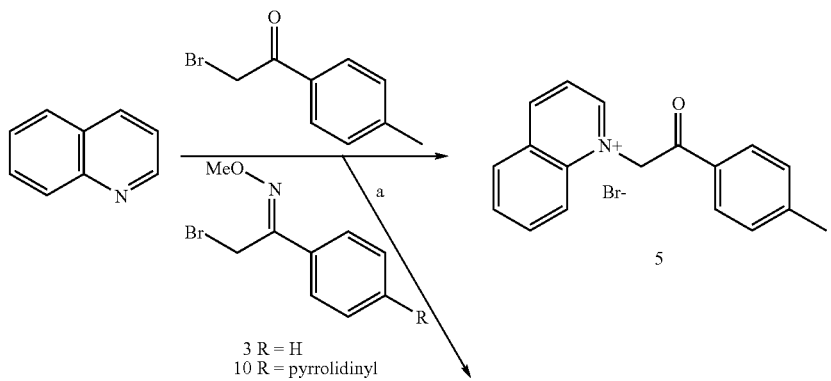

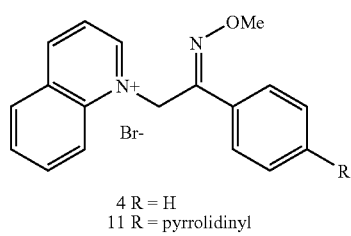

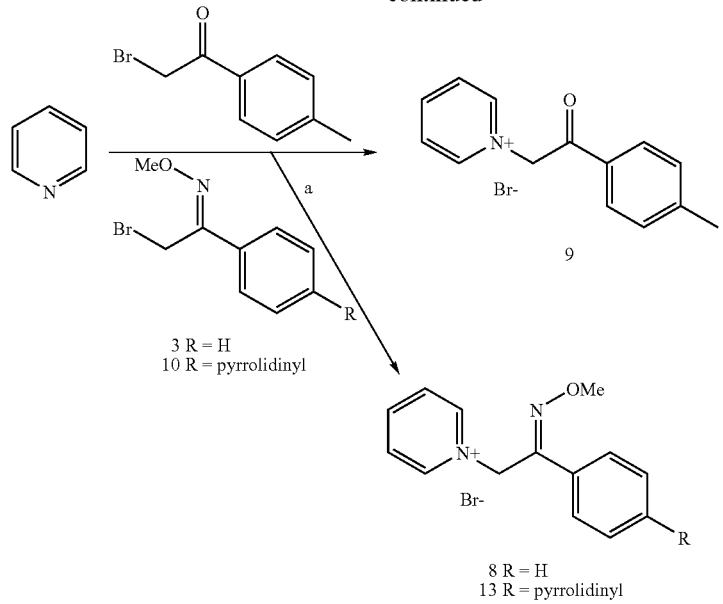

Scheme 2. Reagents and conditions: (a) acetone, reflux, 2 hours to 5 days

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, -ketoglutarate, and -glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, solutions, dispersions, powders, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, solutions, suspensions, dispersions, powders and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid. A further example of a topical application includes liquids that can be used as a mouthwash.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 1 to about 75 mg/kg of body weight per day, such as 3 to about 50 mg per kilogram body weight of the recipient per day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

EXAMPLE 1

2-imino-3-phenacyl-4,5,6,7-tetrahydrobenzothiaole hydrobromide (1) and 2-(p-tolyl)-5,6,7,8-tetrahydrobenzo[d]imidazo[2,1-b]thiazole (2)

The title compounds were prepared by following a procedure reported by Singh (Singh, A.; et al. *Indian J. Chem., Sect. B* 1976, 14B, 997.)

EXAMPLE 2

2-Bromo-1-p-tolylethanone O-methyl oxime (3)

To a solution of 2-bromo-4'-methyl-acetophenone (6.514 g, 27.5 mmol) in methanol at 50° C. was added water until the solution turned slightly cloudy. Methoxylamine hydrochloride (7.037, 85.7 mmol) was added and the mixture was stirred overnight. The solvent was removed under high vacuum and the residue was extracted with EtOAc and dried over $MgSO_4$. The product was purified by flash chromatography on silicagel ($CH_2Cl_2$/hexanes) to give 2 isomers in 87% total yield: 2 isomers in 87% total yield: Z-isomer $^1$H NMR 500 MHz (DMSO-$d_6$) δ 2.33 (s, 3H), 3.83 (s, 3H), 4.62 (s, 2H), 7.26 (dd, 2H, J=1.8, 8.2 Hz), 7.51 (d, 2H, J=7.6 Hz); FABHRMS: found M$^+$, 242.0177 (calcd for $C_{10}H_{13}ONBr$: M$^+$, 242.0175). E-isomer $^1$H-NMR 500 MHz (DMSO-$d_6$) d 2.33 (s, 3H), 3.99 (s, 3H), 4.68 (s, 2H), 7.25 (d, 2H, J=8.2 Hz), 7.61 (d, 2H, J=7.3 Hz); FABHRMS: found M$^+$, 242.0175 (calcd for $C_{10}H_{13}ONBr$: M$^+$, 242.0175).

EXAMPLE 3

1-(2-Methoxyimino-2-p-tolyl-ethyl)-quinolinium bromide (4)

A solution of quinoline and 2-bromo-1-p-tolylethanone O-methyl oxime was stirred refluxed in acetone for 5 days. A precipitate was separated by filtration and rinsed with Et$_2$O to give a light orange solid in 11% yield: mp 285-288° C.; $^1$H NMR 500 MHz (DMSO-d$_6$) δ 2.19 (s, 3H), 4.06 (s, 3H), 6.46 (s, 2H), 7.08 (d, 2H, J=7.9 Hz), 7.37 (d, 2H, J=8.2 Hz), 8.04 (t, 1H, J=7.3 Hz), 8.17 (m, 1H), 8.22 (d, 1H, J=9.2 Hz), 8.32 (m, 1H), 8.44 (d, 1H, J=7.9 Hz), 9.68 (d, 1H, J=8.2 Hz), 9.28 (d, 1H, J=5.8 Hz); Elem. anal. found: C, 61.17; H, 5.18; N, 7.50% (calcd for C$_{19}$H$_{19}$BrN$_2$O: C, 61.47; H, 5.16; N, 7.55%).

EXAMPLE 4

1-(2-Oxo-2-p-tolyl-ethyl)-quinolinium bromide (5)

A solution of quinoline (931 µl, 7.72 mmol) and 2-bromo-4'-methyl-acetophenone (1.828 g, 7.71 mmol) in dichloroethane (6 mL) was refluxed for 1 hour. The resulting brown paste was triturated with ether and filtered. After recristallization from methanol the product was isolated in 46% yield: mp 230-233° C.; $^1$H NMR 500 MHz (DMSO-d$_6$) δ 2.45 (s, 3H), 7.02 (s, 2H), 7.49 (d, 2H, J=7.9 Hz), 8.05 (d, 3H, J=7.9 Hz), 8.21 (m, 1H), 8.32 (dd, 1H, J=6.1, 7.9 Hz), 8.41 (d, 1H, J=9.2 Hz), 8.55 (d, 1H, J=8.2 Hz), 9.45 (d, 1H, J=8.2 Hz), 9.56 (d, 1H, J=5.5 Hz); Elem. anal. found: C, 63.00; H, 4.77; N, 4.09% (calcd for C$_{18}$H$_{16}$BrNO: C, 63.17; H, 4.71; N, 4.09%).

EXAMPLE 5

1-(2-Methoxyimino-2-p-tolyl-ethyl)-1H-quinolin-2-one (6)

To a suspension of 2-hydroxyquinoline (242 mg, 1.63 mmol) in DMF (5 mL) was added NaH (125 mg, 3.13 mmol). After 5 minutes of stirring at room temperature, 2-bromo-1-p-tolylethanone O-methyl oxime (400 mg, 1.65 mmol) was added and the mixture was stirred for 30 additional min. The mixture was poured on ice, extracted with Et$_2$O, and dried over MgSO$_4$. Purification by flash chromatography on silica gel (1% MeOH/CH$_2$Cl$_2$) gave a pure product in 28% yield: mp 129-132° C.; $^1$H NMR 400 MHz (DMSO-d$_6$) δ 2.15 (s, 3H), 4.07 (s, 3H), 5.59 (s, 2H), 6.58 (d, 1H, J=9.2 Hz), 6.98 (d, 2H, J=7.0 Hz), 7.20 (m, 4H), 7.60 (s, 2H), 7.80 (d, 1H, J=8.8 Hz); Elem. anal. found: C, 74.12; H, 5.85; N, 9.00% (calcd for C$_{19}$H$_{18}$N$_2$O$_2$: C, 74.49; H, 5.92; N, 9.14%); MS (ESI) m/z 329.00 (MNa$^+$).

EXAMPLE 6

1-(2-Oxo-2-p-tolyl-ethyl)-1H-quinolin-2-one (7)

To a solution of 2-hydroxyquinoline (296 mg, 2.00 mmol) in DMF (6 mL) was added NaH (93 mg, 2.33 mmol). After 10-15 minutes, a solution of 2-bromo-4'-methyl-acetophenone (622 mg, 2.63 mmol) in DMF (3 mL) was added and the mixture was stirred overnight. Water was added and the mixture was extracted with EtOAc, dried over MgSO$_4$ and purified by flash chromatography on silica gel (MeOH—CH$_2$Cl$_2$ 0:100 to 3:97) to give (11) in 39% yield: mp 173-175° C.; $^1$H NMR 400 MHz (DMSO-d$_6$) δ 2.43 (s, 3H), 5.87 (s, 2H), 6.67 (d, 1H, J=9.3 Hz), 7.26 (t, 1H, J=7.3 Hz), 7.33 (d, 1H, J=8.3 Hz), 7.42 (d, 2H, J=7.8 Hz), 7.52 (t, 1H, J=7.8 Hz), 7.76 (d, 1H, J=7.3 Hz), 8.00 (d, 1H, J=9.8 Hz), 8.04 (d, 2H, J=7.8 Hz); Elem. anal. found: C, 77.70; H, 5.82; N, 5.28% (calcd for C$_{18}$H$_{15}$NO$_2$: C, 77.96; H, 5.45; N, 5.05%).

EXAMPLE 7

1-(2-Methoxyimino-2-p-tolyl-ethyl)-pyridinium bromide (8)

A solution of pyridine (165 µl, 2.05 mmol) and (3) (543 mg, 2.24 mmol) in acetone (3 mL) was refluxed for a day. The solid formed was isolated by filtration and rinsed with Et$_2$O in 84% yield: mp 106-109° C.; $^1$H NMR 400 MHz (DMSO-d$_6$) δ 3.30 (s, 3H), 3.99 (s, 3H), 6.10 (s, 2H), 7.24 (d, 2H, J=5.6 Hz), 7.65 (d, 2H, J=5.9 Hz), 8.13 (m, 2H), 8.60 (m, 1H), 9.07 (s, 2H); FABHRMS: found M$^+$, 241.1340 (calcd for C$_{15}$H$_{17}$ON$_2$: M$^+$, 241.1335).

EXAMPLE 8

1-(2-Oxo-2-p-tolyl-ethyl)-pyridinium bromide (9)

To a solution of 2-bromo-4'-methyl-acetophenone (784 mg, 3.31 mmol) in acetone (7 mL) was added pyridine (243 µl, 3.02 mmol). The mixture was refluxed for 2 hours and the white solid formed was isolated by filtration and rinsed with Et$_2$O in 100% yield: mp 213-214° C.; $^1$H NMR 400 MHz (DMSO-d$_6$) δ 2.45 (s, 3H), 6.50 (s, 2H), 7.48 (d, 2H, J=7.3 Hz), 7.97 (d, 2H, J=7.8 Hz), 8.28 (m, 2H), 8.74 (t, 1H, J=7.3 Hz), 9.03 (d, 2H, J=5.9 Hz); Elem. anal. found: C, 55.46; H, 5.40; N, 4.85% (calcd for C$_{14}$H$_{14}$BrNO ½H$_2$O: C, 55.83; H, 5.02; N, 4.65%).

EXAMPLE 9

2-Bromo-1-(4-pyrrolidin-1-yl-phenyl)-ethanone O-methyl-oxime (10)

To suspension of α-bromo-4-(1-pyrrolidino)acetophenone (Lancaster) (9.432 g, 34.12 mmol) in methanol (100 mL) at 50° C. was added water until the solution turned slightly cloudy (150 mL). Methoxylamine hydrochloride (8.723 g, 102.35 mmol) was added and the mixture was stirred overnight. The methanol was removed under vacuum and the residue was extracted with CH$_2$Cl$_2$ and dried over MgSO$_4$. The product was purified by flash chromatography on silicagel (CH$_2$Cl$_2$/hexanes 1:3) to give (8) as a light orange powder in 60% yield: mp 121-124° C.; $^1$H NMR 400 MHz (DMSO-d$_6$) δ 1.95 (s, 4H), 3.25 (s, 4H), 3.93 (s, 3H), 4.61 (s, 2H), 6.53 (s, 2H), 7.52 (s, 2H); FABHRMS: found M$^+$, 296.0522 (calcd for C$_{13}$H$_{17}$ON$_2$Br: M$^+$, 296.0519).

EXAMPLE 10

1-[2-Methoxyimino-2-(4-pyrrolidin-1-yl-phenyl)-ethyl]-quinolinium bromide (11)

A solution of quinoline (149 µl, 1.26 mmol) and (8) (486 mg, 1.64 mmol) was refluxed in acetone (4 mL) for 5 days. A dark red solid was separated by filtration in 61% yield: mp 178-180° C.; $^1$H NMR 400 MHz (DMSO-d$_6$) δ 1.90 (s, 4H), 3.15 (s, 4H), 3.99 (s, 3H), 6.39 (m, 4H), 7.36 (d, 2H, J=7.3 Hz), 8.05 (t, 1H, J=7.0 Hz), 8.18 (m, 1H), 8.30 (m, 2H), 8.46 (d, 1H, J=8.1 Hz), 9.29 (d, 1H, J=8.1 Hz), 9.65 (d, 1H, J=5.1 Hz); FABHRMS: found M$^+$, 346.1920 (calcd for C$_{22}$H$_{24}$ON$_3$: M$^+$, 346.1914).

EXAMPLE 11

1-[2-Methoxyimino-2-(4-pyrrolidin-1-yl-phenyl)-ethyl]-1H-quinolin-2-one (12)

The title compound was prepared following the examples herein above using suitable reagents, 39% yield: mp 169-171° C.; $^1$H-NMR 400 MHz (DMSO-d$_6$) δ 1.94 (s, 4H), 3.22 (s, 4H), 3.93 (s, 3H), 5.51 (s, 2H), 6.51 (d, 2H), 6.96 (d, 1H), 7.46 (t, 1H), 7.50 (d, 2H), 7.69 (t, 1H), 7.81 (d, 1H), 7.89 (d, 1H), 8.23 (d, 1H).

EXAMPLE 12

1-[2-Methoxyimino-2-(4-pyrrolidin-1-yl-phenyl)-ethyl]-pyridinium bromide (13)

The title compound was prepared following the examples herein above using suitable reagents, 60% yield: mp 194-196° C.; $^1$H-NMR 400 MHz (DMSO-d$_6$) δ 1.95 (s, 4H), 3.24 (s, 4H), 3.92 (s, 3H), 5.96 (s, 2H), 6.52 (d, 2H), 7.58 (d, 2H), 8.12 (t, 2H), 8.59 (t, 1H), 8.07 (d, 1H).

The ability of a compound of the invention to act as Chemo-preventive agents may be determined using pharmacological models which are well known to the art, or using tests described below.

EXAMPLE 13

Apoptosis Assays

Protection of Thymocytes from γ-Radiation

Thymocytes were harvested from young C57Bl/6 mice and cultured at 37° C. in 5% $CO_2$ in RPMI 1640 containing 10% FBS, 1% Penicillin/Streptomycin (Gibco BRL, Rockville, Md.). Thymocytes were plated at a density of $10^7$ cells/mL and pre-incubated with 5-10 μM of test compounds, 1, 2, 4, and 11 (from 10 mM

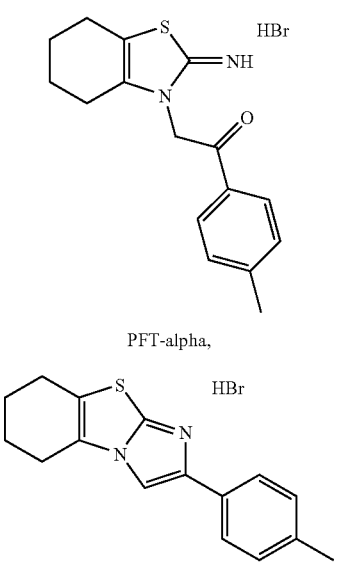

Figure 2:
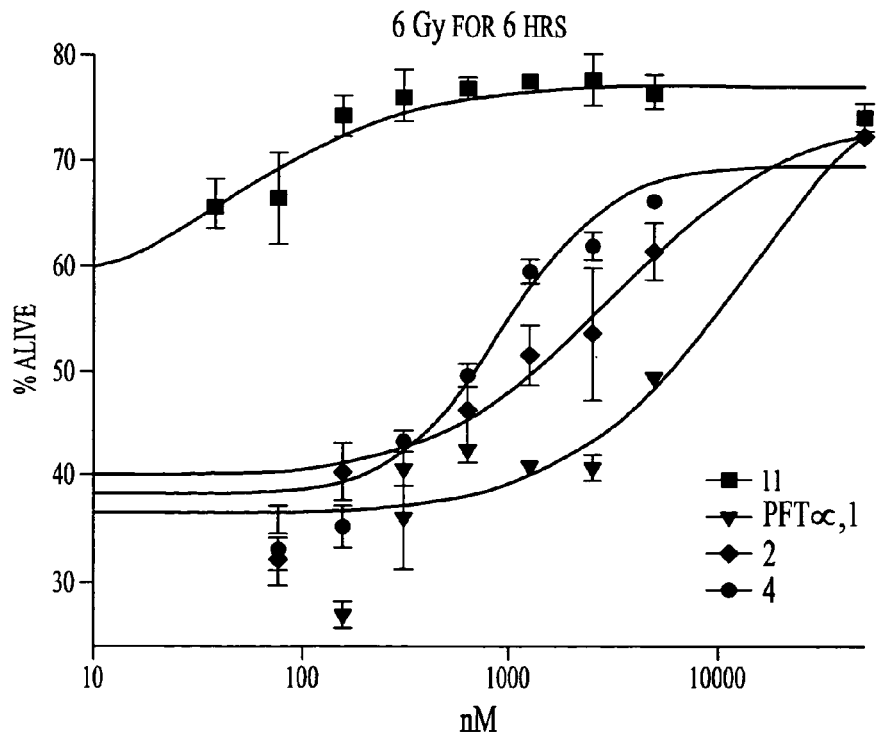
FIG. 2 is a graphical representation of the titration of 1 (PFTα), 2, 4, and 11.

PFT-alpha, stock in DMSO) for 30 minutes before induction of apoptosis. Apoptosis was induced with 5 μM dexamethasone or by exposure to 6 Gy gamma radiation. After 6 hours, cell apoptosis was assayed by propidium iodide (PI) and 3,3' dihexyloxacarbocyanine iodide ($DiOC_6$) staining. The cells were removed from the plate and incubated for 30 minutes in medium with 40 nM $DiOC_6$ and 5 μg/mL PI and then analyzed by flow cytometry in a FACS caliber (Beckton-Dickinson, San Jose, Calif.). Viable cells had high $DiOC_6$ (FL-1) and low PI (FL-3), whereas apoptotic cells had low $DiOC_6$ (FL-1) and low PI (FL-3). To evaluate the $IC_{50}$s the thymocytes were pre-exposed to graded concentrations of selected compounds for 30 min and then apoptosis was induced with 5 μM dexamethasone. After 6 hours the cells were harvested and stained as above. The results are illustrated in FIGS. 1 and 2

$IC_{50}$ Determination

The concentration ($IC_{50}$) of each compound that inhibited dexamethasone-induced cell death by 50% was determined by nonlinear regression fitting of the data to a one-site model. Pseudo Hill slopes were determined by nonlinear regression fit of the data to a sigmoidal dose-response equation (variable slope): % viability=minimum %/viability+(maximum−minimum % viability)/[1+10(log $IC_{50}$−X)$^n$], where X is the logarithm of inhibitor concentration, and n is the pseudo Hill slope and the maximum and minimum % viability were experimentally determined after dexamethasone exposure and drug treatment. $IC_{50}$ values and 95% confidence intervals (CI) were derived from the sigmoid fits to the percent control transformed data shown using GraphPad Prism version 4.0b for Macintosh (GraphPad Software, San Diego, Calif.).

The results from the assays of representative compounds are illustrated in Table 4

TABLE 4

In vitro cytoprotection activity of quaternary salts and related compounds

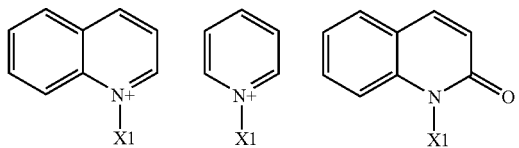

| X1 = | (quinolinium) | (pyridinium) | (2-quinolinone) |
|---|---|---|---|
| 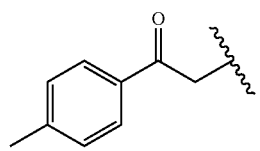 | 5<br>$EC_{50} > 10 ≅ M$ | 9<br>$EC_{50} > 10 ≅ M$ | 7<br>$EC_{50} > 10 ≅ M$ |
| 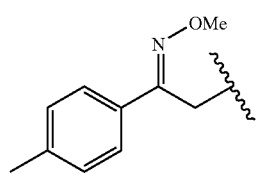 | 4<br>$EC_{50} = 0.35 ≅ M$<br>(0.27-0.44) | 8<br>$EC_{50} = 5.1 ≅ M$<br>(3.9-6.6) | 6<br>$EC_{50} > 10 ≅ M$ |

TABLE 4-continued

In vitro cytoprotection activity of quaternary salts and related compounds

| X1 = | 11 | 13 | 12 |
|---|---|---|---|
| (4-pyrrolidinylphenyl methoxime-CH₂- group) | quinolinium $EC_{50} = 0.013 \cong M$ (0.075-0.024) | pyridinium $EC_{50} = 0.28 \cong M$ (0.17-0.46) | 2-oxo-quinolinyl $EC_{50} > 10 \cong M$ |

EXAMPLE 14

Pharmaceutical Dosage Forms

The following illustrate representative pharmaceutical dosage forms, containing a compound of formula (I) ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

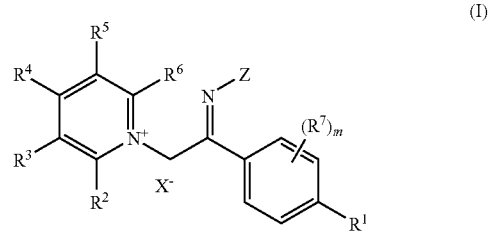

(I)

wherein $R^1$ is —$N(R^b)(R^c)$, $(C_3-C_7)$cycloalkyl, aryl, or heteroaryl, or a 5-6 membered heterocyclic ring, optionally comprising 1, 2, or 3 —$N(R^b)$—, nonperoxide O or S atoms;

wherein $R^1$ is optionally substituted with 1, 2, 3, 4, or 5, halo, —$CF_3$, hydroxy, cyano, ($C_1$-$C_6$)alkyl, ($C_1$-$C_6$)alkoxy, ($C_2$-$C_7$)alkanoyl, ($C_2$-$C_7$)alkanoyloxy, —$CO_2R^a$, ($C_3$-$C_7$)cycloalkyl, ($C_2$-$C_6$)alkanoyl, ($C_2$-$C_6$)alkenyl, or aryl groups;

$R^2$, $R^3$, $R^4$, $R^5$, and $R^6$ are independently hydrogen, halo, hydroxy, cyano, —$N(R^b)(R^c)$, $S(R^a)$, —$NO_2$, ($C_1$-$C_6$)alkyl, ($C_1$-$C_6$)alkoxy, ($C_2$-$C_6$)alkynyl, ($C_2$-$C_6$)alkenyl, ($C_2$-$C_7$)alkanoyl, ($C_2$-$C_7$)alkanoyloxy, or ($C_3$-$C_7$)cycloalkyl; or either $R^2$ and $R^3$ or either $R^3$ and $R^4$ taken together with the atoms to which they are attached form a benzo ring, optionally substituted with 1, 2, 3, or 4 $R^6$ groups, or either $R^2$ and $R^3$ or either $R^3$ and $R^4$ are a 3, 4, or 5 membered alkylene chain (e.g. —$CH_2$—, —$CH_2CH_2$—, —$CH_2CH_2CH_2$—, or —$CH_2CH_2CH_2CH_2$—) 3, 4, or 5 membered alkenylene, or methylenedioxy that is fused to the ring;

each $R^7$ is independently hydrogen, halo, hydroxy, cyano, —$N(R^b)(R^c)$, —$S(R^a)$, —$NO_2$, ($C_1$-$C_6$)alkyl, ($C_1$-$C_6$)alkoxy, ($C_2$-$C_6$)alkynyl, ($C_2$-$C_6$)alkenyl, ($C_2$-$C_7$)alkanoyl, ($C_2$-$C_7$)alkanoyloxy, or ($C_3$-$C_7$)cycloalkyl;

wherein each $R^a$ is independently hydrogen, ($C_1$-$C_3$)alkyl, phenyl, benzyl, or phenethyl; and wherein $R^b$ and $R^c$ are each independently hydrogen, ($C_1$-$C_3$)alkyl, ($C_2$-$C_4$)alkanoyl, phenyl, benzyl, or phenethyl; or $R^b$ and $R^c$ together with the nitrogen to which they are attached are a 5 or 6 membered heterocyclic ring, optionally comprising 1, 2, or 3 —$N(R^a)$—, non-peroxide O or S atoms, Z is —$OR^a$, —$SR^a$, or —$N(R^{b)(Rc)}$; m is 0, 1, 2, 3, or 4;
$X^-$ is a pharmaceutically acceptable counterion.

2. The compound of claim 1, wherein $R^1$ is —$N(R^b)(R^c)$, or aryl.

3. The compound of claim 1, wherein $R^1$ is —$N(R^b)(R^c)$, or phenyl.

4. The compound of claim 1, wherein $R^1$ is pyrrolidinyl, piperizinyl, piperidinyl, or morpholinyl.

5. The compound of claim 1, wherein $R^1$ is pyrrolidinyl.

6. The compound of claim 1, wherein $R^2$ is hydrogen, ($C_1$-$C_4$)alkyl, ($C_1$-$C_4$)alkoxy, halo, hydroxy, cyano, or —$N(R^b)(R^c)$.

7. The compound of claim 1, wherein $R^2$ is hydrogen.

8. The compound of claim 1, wherein $R^3$ is hydrogen, ($C_1$-$C_4$)alkyl, ($C_1$-$C_4$)alkoxy, halo, hydroxy, cyano, or —$N(R^b)(R^c)$.

9. The compound of claim 1, wherein $R^3$ is hydrogen.

10. The compound of claim 1, wherein $R^4$ is hydrogen, ($C_1$-$C_4$)alkyl, ($C_1$-$C_4$)alkoxy, halo, hydroxy, cyano, or —$N(R^b)(R^c)$.

11. The compound of claim 1, wherein $R^4$ is hydrogen.

12. The compound of claim 1, wherein $R^5$ is hydrogen, ($C_1$-$C_4$)alkyl, ($C_1$-$C_4$)alkoxy, halo, hydroxy, cyano, or —$N(R^b)(R^c)$.

13. The compound of claim 1, wherein $R^5$ is hydrogen.

14. The compound of claim 1, wherein $R^6$ is hydrogen, ($C_1$-$C_4$)alkyl, ($C_1$-$C_4$)alkoxy, halo, hydroxy, cyano, or —$N(R^b)(R^c)$.

15. The compound of claim 1, wherein $R^6$ is hydrogen.

16. The compound of claim 1, wherein $R^2$ and $R^3$ taken together with the atoms to which they are attached form a benzo ring.

17. The compound of claim 1, wherein $R^3$ and $R^4$ taken together with the atoms to which they are attached form a benzo ring.

18. The compound of claim 1, wherein $R^7$ is hydrogen ($C_1$-$C_4$)alkyl, ($C_1$-$C_4$)alkoxy, halo, hydroxy, cyano, —$N(R^b)(R^c)$.

19. The compound of claim 1, wherein $R^7$ is fluoro.

20. The compound of claim 1, wherein $R^7$ is hydrogen.

21. The compound of claim 1, wherein m is 0, 1, 2.

22. The compound of claim 1, wherein $R^a$ is hydrogen, ($C_1$-$C_4$)alkyl, phenyl, or benzyl.

23. The compound of claim 1, wherein $R^b$ is hydrogen, ($C_1$-$C_4$)alkyl, phenyl, acetyl, propionyl, butanoyl, or benzyl.

24. The compound of claim 1, wherein $R^b$ is hydrogen, ($C_1$-$C_4$)alkyl, phenyl, acetyl, propionyl, butanoyl, or benzyl.

25. The compound of claim 1, wherein —$N(R^b)(R^c)$, is pyrrolidinyl, piperizinyl, piperidinyl, or morpholinyl.

26. The compound of claim 1, wherein —$N(R^b)(R^c)$, is pyrrolidinyl.

27. The compound of claim 1, wherein —$N(R^b)(R^c)$, is morpholinyl.

28. The compound of claim 1, wherein Z is hydroxy, methoxy, ethoxy, —$NH(OCH_3)$, or —$NH(OCH_2CH_3)$.

29. The compound of claim 1, wherein $X^-$ is chloride, bromide, hydroxide, sulfate, phosphate, carbonate, acetate, or citrate.

30. A pharmaceutical composition comprising a compound of claim 1 in combination with a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,816,352 B2 | |
| APPLICATION NO. | : 11/885463 | |
| DATED | : October 19, 2010 | |
| INVENTOR(S) | : Dennis A. Carson et al. | |

It is certified that error appears in the above-identified patent and that said Letters Patent is hereby corrected as shown below:

Title page 2, under "Other Publications", in column 1, line 21, delete "[1,2-a}" and insert -- [1,2-a] --, therefor.

Title page 2, under "Other Publications", in column 2, line 9, delete "Journale" and insert -- Journal --, therefor.

Title page 2, under "Other Publications", in column 2, line 12, delete "pBromophenacyl" and insert -- p-Bromophenacyl --, therefor.

Title page 2, under "Other Publications", in column 2, line 25, delete "Journale" and insert -- Journal --, therefor.

Title page 2, under "Other Publications", in column 2, line 25, delete "Beligique," and insert -- Belgique, --, therefor.

In column 1, line 21, delete "Clin." and insert -- Clin., --, therefor.

In column 2, line 47, delete "$R^1$," and insert -- $R^2$, --, therefor.

In column 4, line 14, delete "substituents" and insert -- substituents. --, therefor.

In column 6, line 54, delete "11" and insert -- 109 --, therefor.

In column 14, line 52, delete "silicagel" and insert -- silica gel --, therefor.

In column 15, lines 15-16, delete "recristallization" and insert -- recrystallization --, therefor.

In column 15, line 50, delete "(MeOH—$CH_2Cl_2$" and insert -- (MeOH/$CH_2Cl_2$ --, therefor.

Signed and Sealed this
First Day of February, 2011

David J. Kappos
*Director of the United States Patent and Trademark Office*

CERTIFICATE OF CORRECTION (continued)
U.S. Pat. No. 7,816,352 B2

In column 16, lines 26-27, delete "silicagel" and insert -- silica gel --, therefor.

In column 18, line 16, delete "2" and insert -- 2. --, therefor.

In column 21, line 30, in Claim 1, delete "—N($R^{b)(Rc}$);" and insert -- —N($R^b$)($R^c$); --, therefor.